United States Patent
Goldenberg

(10) Patent No.: US 8,894,586 B2
(45) Date of Patent: Nov. 25, 2014

(54) SNARECOIL RETRIEVAL DEVICE FOR CAPTURING AND RETRIEVING A SPECIMEN

(76) Inventor: Alec S. Goldenberg, New York, NY (US)

(*) Notice: Subject to any disclaimer, the term of this patent is extended or adjusted under 35 U.S.C. 154(b) by 361 days.

(21) Appl. No.: 13/323,115

(22) Filed: Dec. 12, 2011

(65) Prior Publication Data

US 2012/0150066 A1 Jun. 14, 2012

Related U.S. Application Data

(60) Provisional application No. 61/422,339, filed on Dec. 13, 2010.

(51) Int. Cl.
*A61B 10/02* (2006.01)
*A61B 17/3205* (2006.01)
*A61B 17/3207* (2006.01)

(52) U.S. Cl.
CPC ....... *A61B 10/0275* (2013.01); *A61B 17/32056* (2013.01); *A61B 17/320783* (2013.01)
USPC ........................................................ 600/567

(58) Field of Classification Search
CPC ................................................. A61B 10/0266
USPC ................................................. 600/564, 567
See application file for complete search history.

(56) References Cited

U.S. PATENT DOCUMENTS

| | | | |
|---|---|---|---|
| 3,605,721 A | 9/1971 | Hallac | |
| 5,522,398 A | 6/1996 | Goldenberg et al. | |
| 5,634,473 A | 6/1997 | Goldenberg et al. | |
| 6,015,391 A * | 1/2000 | Rishton et al. | 600/567 |
| 6,033,369 A * | 3/2000 | Goldenberg | 600/567 |
| 6,569,176 B2 * | 5/2003 | Jesseph | 606/167 |
| 7,278,970 B2 * | 10/2007 | Goldenberg | 600/564 |
| 7,338,456 B2 * | 3/2008 | Goldenberg | 600/564 |
| 7,384,400 B2 * | 6/2008 | Goldenberg | 600/564 |
| 7,455,645 B2 * | 11/2008 | Goldenberg | 600/564 |
| 7,608,048 B2 * | 10/2009 | Goldenberg | 600/564 |
| 7,608,049 B2 * | 10/2009 | Goldenberg | 600/564 |
| 7,621,923 B2 | 11/2009 | Goldenberg | |
| 7,731,667 B2 * | 6/2010 | Goldenberg | 600/567 |
| 8,398,566 B2 * | 3/2013 | Goldenberg | 600/567 |
| 2003/0114773 A1 * | 6/2003 | Janssens | 600/564 |
| 2007/0142744 A1 * | 6/2007 | Provencher | 600/562 |
| 2008/0154150 A1 * | 6/2008 | Goldenberg | 600/564 |
| 2008/0234699 A1 | 9/2008 | Oostman, Jr. et al. | |
| 2008/0281223 A1 * | 11/2008 | Goldenberg | 600/567 |
| 2009/0082697 A1 | 3/2009 | Goldenberg | |

* cited by examiner

*Primary Examiner* — Sean Dougherty
*Assistant Examiner* — Michael C Stout
(74) *Attorney, Agent, or Firm* — Leason Ellis LLP

(57) ABSTRACT

A retrieval device for collecting a specimen includes an outer cannula member having an inner lumen and an inner member received within the inner lumen such that the inner member can rotate relative to the outer cannula. The device also includes first and second snarecoil elements that are formed as part of the inner member. Each snarecoil element has an arcuate shape and is attached to an inner surface of the outer cannula. The snarecoil elements being deformable such that rotation of the inner member relative to the outer catheter results in the snarecoil elements collapsing toward a center of the outer cannula member resulting in either the tissue specimen being captured between the two snarecoil elements in one embodiment or being sheared by the two snarecoil elements in another embodiment.

21 Claims, 4 Drawing Sheets

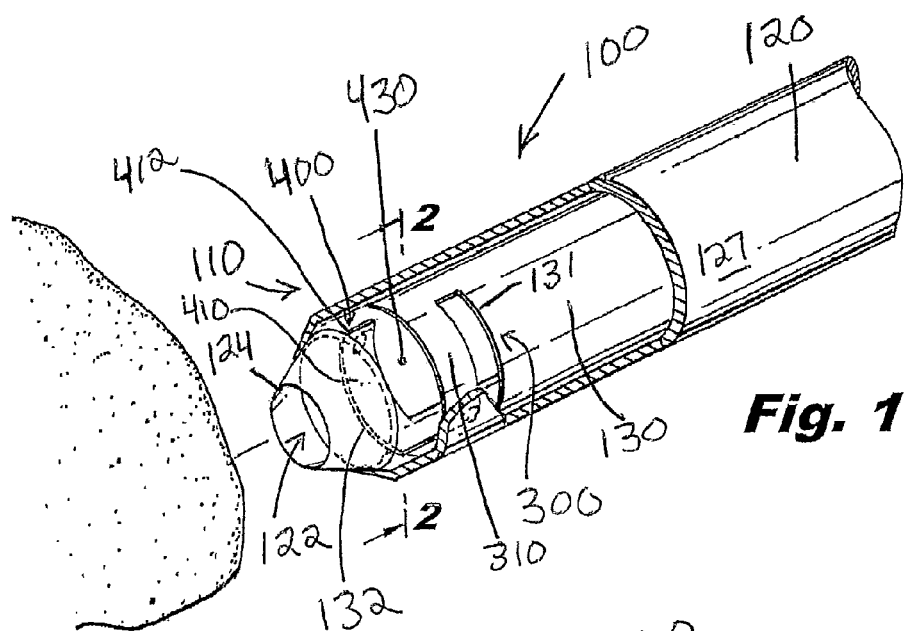
*Fig. 1*
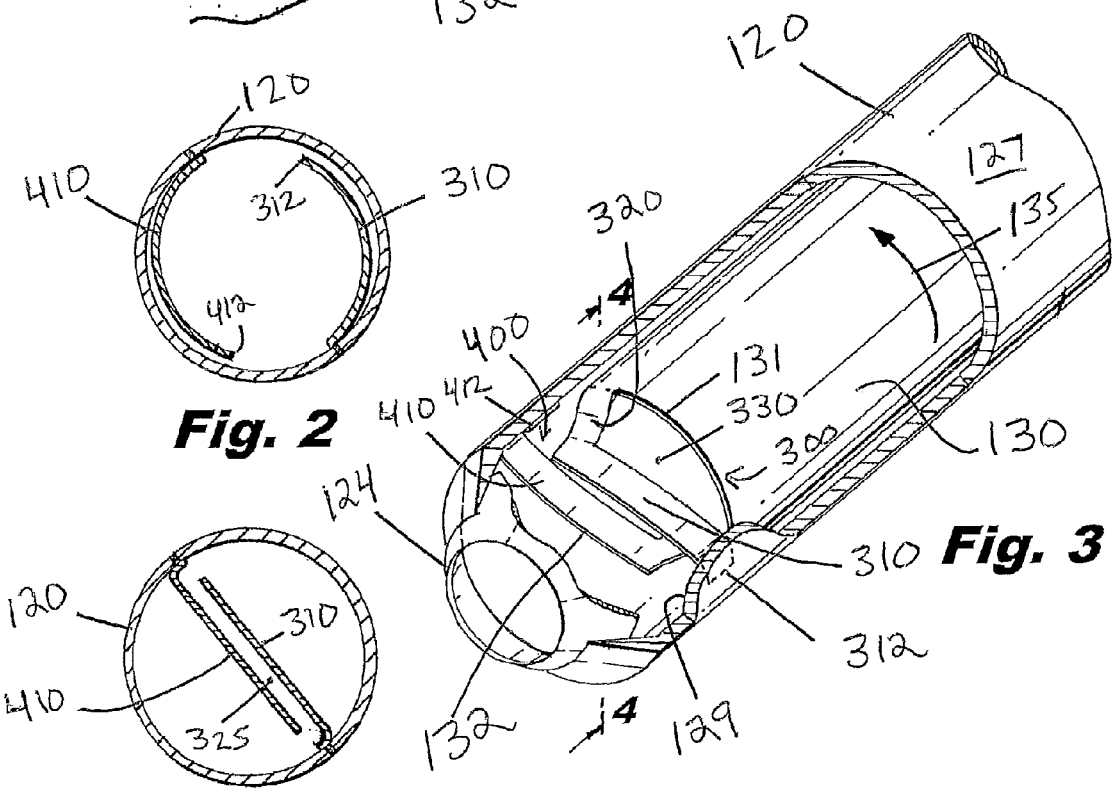
*Fig. 2*
*Fig. 3*
*Fig. 4*

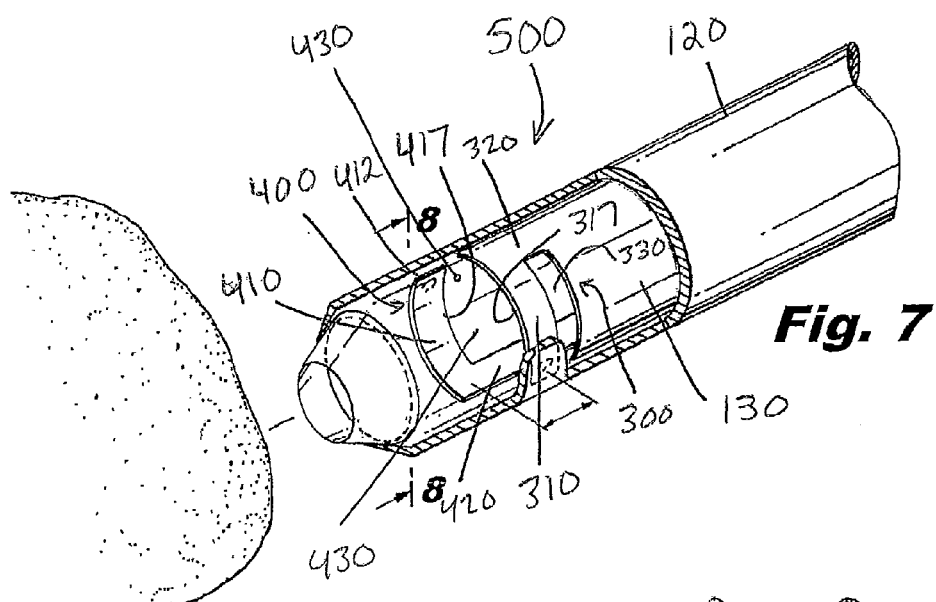
Fig. 7
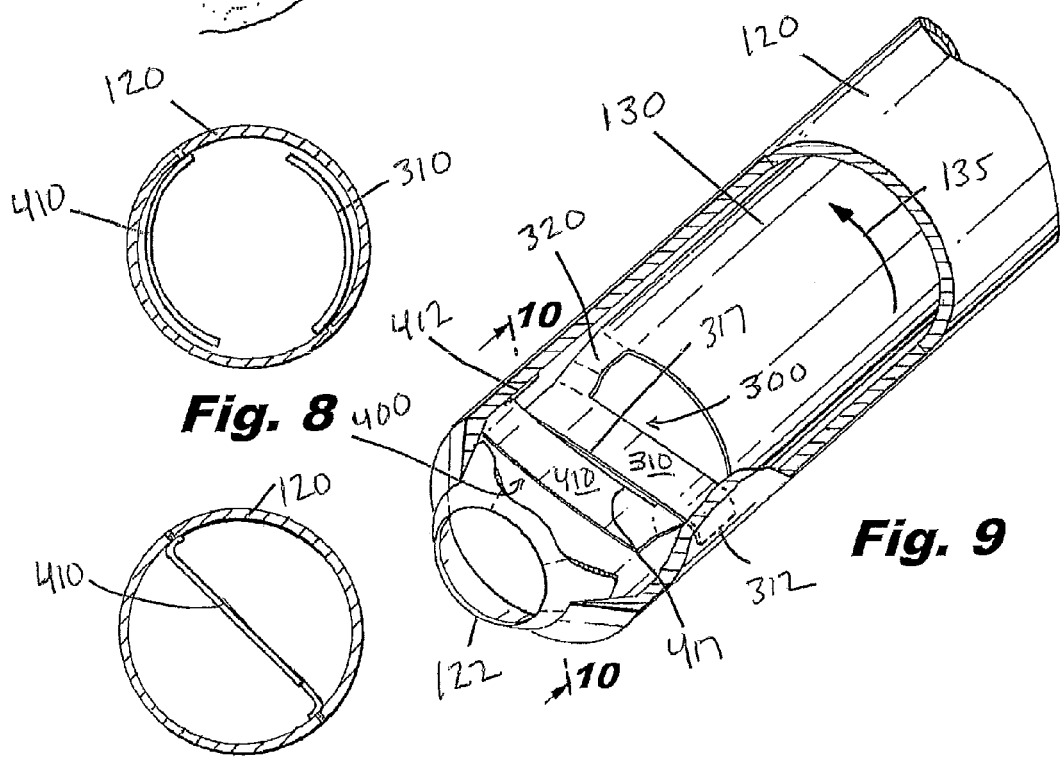
Fig. 8
Fig. 9
Fig. 10

SNARECOIL RETRIEVAL DEVICE FOR CAPTURING AND RETRIEVING A SPECIMEN

CROSS REFERENCE TO RELATED APPLICATION

The present application claims priority to U.S. patent application Ser. No. 61/422,339, filed Dec. 13, 2010, which is hereby incorporated by reference in its entirety.

TECHNICAL FIELD

The present invention relates to a surgical instrument, typically known as a retrieval device sometimes configured as a biopsy needle for retrieving a target specimen and more particularly, relates to a minimally invasive retrieval device sometimes configured as a specimen capturing biopsy needle that allows an operator to manipulate the retrieval mechanism for efficient specimen capture and/or specimen cutting.

BACKGROUND

Patients are increasingly undergoing more intravascular and minimally invasive procedures as alternatives to open surgical procedures. In particular, needle biopsy procedures are favored over open biopsy procedures if feasible. Less invasive procedures employ a variety of catheters or other devices which are positioned in vascular, abdominal, pulmonary, or urologic spaces with the goal of manipulating, cutting, and/or stabilizing structures at a distance from the operator. A variety of tissue retrieval and biopsy devices or needles are employed to recover tissue samples for analysis. As every procedure has a certain failure rate, there will be by definition cases or instances where a component of the device separates and is difficult to retrieve or a material is placed or separates from a device and needs to be captured and removed. In addition there will be instances in which standard biopsy devices return inadequate amounts of poorly preserved tissue limiting accurate pathologic interpretation.

In the setting of vascular procedures, a catheter segment, wire or balloon segment may become dislodged and must be recovered. In the setting of minimally invasive surgical procedures, a device component, suture clip, or staple, may be lodged in a small cavity or region where retrieval might be compromised or difficult with typical minimally invasive surgical devices. Percutaneous or laparascopic biopsy procedures may be compromised by the recovery of small tissue samples if the capturing or cutting mechanism performs poorly. Occasionally no sample is recovered if the capturing mechanism completely fails. In the practice of biliary endoscopy and urology, stents and other catheters or other dislodged components may require subsequent retrieval.

Retrieval of retained device elements or materials through open direct explorations, can be overly invasive and traumatic, and inconsistent with the basic principles of reducing direct trauma through minimally invasive procedures. Therefore, minimally invasive devices and techniques have been developed to retrieve unintentionally dislodged objects from the body.

Moreover certain pathologic materials, such as thrombi, emboli or stone excrescences, can be difficult to capture within delicate small spaces and require devices that can easily and efficiently capture or grab them for retrieval. The recoverability of a biopsy specimen may highly depend on the mechanical characteristic of the tissue that is being biopsied. The use of retrieval devices for the removal of stones within ureters, or bladder or within the biliary system are examples of the application of retrieval devices to remove pathologic materials that previously required open procedures, which often were associated with significant morbidities.

The development of stones within the ureters can result in renal insufficiency and recurrent infections. Removal of the stones can reverse obstructive phenomena, decrease pain, improve renal function and decrease recurrent infections. Biliary stones dislodged from the gallbladder can result in recurrent biliary obstruction, jaundice, pain and infection which can be alleviated by removal of the obstructing stone elements.

The development of a thrombus or dislodgment of an embolus within a vascular space results in downstream ischemia which can have profound physiologic consequences. If such an event occurs within the central nervous system, focal brain ischemia ensues resulting in the clinical manifestations of a stroke. The development of a thrombus or the dislodgment of an embolus into the peripheral vasculature can result in limb ischemia. Thrombi that develop in the coronary arteries result in myocardial infarctions.

Recovery of tissue specimens through the use of retrieval devices such as percutaneous, endoscopic or laparoscopic specimen capturing biopsy needles, provides critical information that guides treatment decisions. Efficient recovery of adequate amounts of tissue is required for pathologists to render reliable histopathologic diagnoses.

Retrieval devices have been developed and employed for the recovery of tissue specimens, vascular thrombi, or emboli. The process of removing a tissue specimen is referred to as a biopsy procedure. The procedure that removes a thrombosis is called an embolectomy and has been used by Interventional Radiologists and Vascular surgeons therapeutically, for sometime. Removing these thrombi or emboli with minimally invasive procedures can be efficient and potentially less morbid then open direct procedures. Therefore, retrieval devices designed to remove a variety of foreign bodies and tissue components have been developed and are routinely employed in the practice of medicine. Addressing design aspects of the retrieval mechanisms can increase the performance of the devices and provide clinicians with better tools for more reliably retrieving foreign bodies emboli and diagnostic tissue specimens.

A number of foreign body retrieval devices have been designed and have entered the commercial marketplace. While a number of different devices are available, there are generally four types of foreign body retrieval devices that have gained more widespread popularity and use. In particular, the four types of devices can be referred to and identified as the (1) Gooseneck design snare; (2) Texan snare; (3) En Snare; and (4) the In Time retrieval device.

A review of some of the more common prior art devices reveals that the devices can be divided into three designs categories. The first type of design is a device that incorporates single snare or multiple looped snares that project from a catheter. The diameter of the snare loop or loops is controlled by advancing or retracting the catheter "over" the looped wire system or alternatively by advancing or retracting the wire system within a relatively stationary catheter system. The wire loop or loops are manipulated or stabilized by the operator by a long wire which is connected to the loop or snare and extends distally to the proximal portion of a catheter system. Examples of this type of system include the Amplatz gooseneck system or the En Snare system marketed by Merit.

The second type of design includes a mesh or basket assembly which is defined by multiple loops or struts that can be deployed through a catheter system. The basket or mesh system is attached to a wire which extends through the catheter system. The proximal aspect of the wire is available to the operator at the proximal portion of the catheter. The geometry and therefore activation of a mesh system is controlled by varying the relative positions of the catheter meshed/wired structure. In some sense the relationship and control of the geometry of the wire loops is similar to the first type of device in that a catheter initially constrains and keeps the wire mesh system from expanding as it is retained within the catheter lumen. Once the basket or mesh system is advanced through the catheter, it may expand to its fully deployed geometry.

After engaging a foreign body, the basket or mesh system can be retrieved by uniformly pulling back on the wire and catheter without changing the longitudinal relationship of the two components, hopefully with the foreign body engaged. Alternatively, the deployment catheter can be partially pushed over the mesh system to change the geometry of the system and to produce a capturing force along the surface of the foreign body. After such a maneuver, the longitudinal relationship of the activated mesh system and catheter are maintained and the system is removed hopefully with the foreign body securely captured.

A third type of device incorporates a multi-wired basket-like structure located at the end of a catheter system. The In Time retrieval system marketed by Boston Scientific is an example of this type of system. A wire mesh or multi-strutted system is attached to the tip of a microcatheter. The mesh or basket element is not designed to be deployed from within the catheter system but is attached to its most distal end. The geometry of the mesh capturing system is controlled by a core wire that passes through the catheter system and attaches to the distal aspect of the mesh or basket system. The capturing element is "opened up" that is the spaces between the wires or struts are increased by decreasing the longitudinal length of the basket system by pulling the core wire proximally. Once a foreign body is engaged within the capturing mesh wire system the spaces between the capturing struts can be decreased by elongating the wire system by advancing the core wire forward or distally. The mesh system can also be rotated by rotating the core wire, sometimes increasing the device's ability to capture a foreign body. More specifically, the In Time product is made of a Nitinol braided microcatheter shaft, a radiopaque retrieval basket and a steerable Nitinol core wire.

There are a number of shortcomings in the design of the above-described conventional devices and their application in clinical practice, which limits their effectiveness and/or simplicity.

The success of the retrieval procedure depends on the ability of the retrieval device to efficiently and reliably capture the foreign material. The initial steps of the procedure require that the retrieval device must come in contact with the foreign material in a way that allows the device to engage it or grab it. The efficiency of that step depends on the ability of the operator to control the position and contour of the wires/mesh in relation to the foreign material. The design of the first type of retrieval devices makes it difficult to change the contour or geometry of the snare loop since manipulation of a wire at the proximal end of the catheter system must be translated into contour changes of the loop(s) at the distal end of the device. Rotating the internal wire at the proximal end of the catheter may not efficiently translate into controllable movements of the snare loop that will precisely localize the loop into a position adjacent to a foreign material.

As regards, the second or third types of foreign body retrieval devices in which the capturing element is a mesh or basket-like configuration, individual control of any particular wire loop within the mesh is more problematic. The mesh system provides multiple "openings" through which a material potentially will be engaged. However, the fact that there is an increased number of notches or gaps in which a foreign material may enter only increases the probability that such an event will occur and does not guarantee it. The engagement is a relatively chance event and not necessarily driven by a precise alignment and control of a wire loop(s) in the region of the foreign material. Also some of these designs depend on converting longitudinal translation of the core wire into the precise localization of a wire or multiple wires which can be technically challenging.

The ability to engage a foreign material and capture it within the central portion of the basket structure can be compromised by the complicated woven structure of the basket wires which may impede transit and positioning of the foreign material within the basket's central portion.

The ability of the foreign material to remain securely engaged with the retrieval device depends not only on the force to which the material is exposed but the surface area of the grabbing or engaging element which is in contact with the foreign material.

The first type of device generally has one or a few snare loops that engage the foreign material. When the loop size is decreased, the foreign material is pushed against either the tip or distal side of the catheter. Although bringing the foreign material adjacent to the side of the catheter increases the surface area that can contact the material, this type of orientation usually only applies to devices with a single capturing loop and the precision and geometry of engagement may not maximize the amount of surface area that comes into contact with the foreign material.

In devices that are either of the second or third types the surface area of engagement is limited to the surface area described by one or multiple relatively small diameter wires. If a foreign material is engaged between two wires, there will be minimal surface area in contact with the foreign material thereby compromising the reliability of the capture. Of course, if the foreign material finds its way into multiple notches or gaps, the total contact surface area will increase and the engagement will be more secure. However the second possibility may only occur by chance, since as above, it is difficult to precisely direct such a mesh element to engage a foreign material at multiple sites.

Although these types of devices can be useful in certain applications, other devices that maximize their ability to precisely, efficiently capture foreign and pathologic objects as well as tissue samples may be more useful to the interventionalist.

Tissue specimen retrieval devices, often referred to as biopsy needles, are configured to retrieve a representative specimen of tissue for pathologic analysis. Tissue specimens also may be used for immunohistochemical studies as well as molecular evaluations. It is therefore important to recover substantial specimens that are representative of the structure and morphology of the underlying tissue. Most biopsy needles are tubes that are designed to retrieve the specimen within the lumen of the device. The earliest designs included no ancillary mechanisms to capture the specimen once it entered the lumen of the needle. Later designs have incorporated capturing mechanisms to secure the specimen in the lumen to help ensure that an adequate specimen is recovered.

Two types of designs have been employed in soft tissue biopsy needle devices to facilitate the consistent retrieval of adequate specimens. One design includes opposing curved plates that function as a pinching or "biting" mechanism to cut a small segment of tissue which is retained within the opposed plates until they are mechanically unopposed freeing the specimen for recovery. The second design, which is commonly employed, in the great majority of soft tissue biopsy needles, includes a shaft into which a tissue component prolapses and then is cut for retrieval by a biopsy needle tube. The construction is commonly referred to as a "true cut" biopsy needle.

Each of these designs has there disadvantages. Biopsy needles which employ a biting mechanism to secure the specimen for retrieval usually provide limited samples for histopathologic evaluation which sometimes compromises the pathologist's ability to provide the clinician with a definitive diagnosis. Alternatively, the "true cut" design may provide a less than representative tissue sample since the tissue capturing mechanism, by definition, does not provide a full core of tissue.

Newer soft tissue biopsy needles have focused on providing specimen capturing designs that acquire substantial amounts of specimens to maximize the pathologist's ability to render a definitive diagnosis. These soft tissue biopsy needles are designed to capture a full core of a specimen. One such needle is marketed as the BioPince device. It incorporates a flexible component that severs the specimen at the needle tip and retains it within the lumen of the needle to facilitate recovery of the specimen.

Another specimen capturing technology that may be applicable to the construction and design of tissue biopsy needles is the Snarecoil technology. Snarecoils have generally been configured as helical coils whose diameters are reduced by rotation. As the diameter of these capturing coils is reduced they secure a sample in the lumen of a biopsy needle.

The present applicant has a number of issued patents that are directed to various snarecoil designs. For example, snarecoil designs are disclosed in U.S. Pat. Nos. 7,621,923; 7,608,049; 7,608,048; 7,455,645; 7,384,400; 7,338,456; 7,278,970; 6,015,391; 5,634,473; and 5,522,398, each of which is hereby incorporated by reference in its entirety. While these snarecoil designs perform their intended functions, there is a need in particular settings for a different snarecoil design that is more particularly suited for grasping, cutting or deforming certain tissues that tend to collapse when pressure is applied by a conventional snarecoil.

The reduction in the diameter of presently available Snarecoil designs/configurations is limited since many rotations of the coil assembly is required to reduce the diameter of the coil configuration to a minimum. In addition the helical design, by definition, does not cause the coil to pass through the central position of the lumen of the biopsy needle. Since soft tissue capturing coil assemblies must be capable of completely reducing their diameters and/or transecting the central portion of the needle lumen, needle performance is compromised when helical snarecoil capturing mechanisms are incorporated into soft tissue biopsy needles. As a result, in practice, soft tissue biopsy needles that contain helical Snarecoil capturing assemblies do not capture and recover specimens in a consistent fashion. Therefore, to overcome these deficiencies new capturing mechanism designs have been devised.

Other features and advantages of the present invention will be apparent from the following detailed description when read in conjunction with the accompanying drawings.

SUMMARY

In one embodiment, a retrieval device for collecting a specimen includes an outer cannula member having an inner lumen and an inner member received within the inner lumen such that the inner member can rotate relative to the outer cannula. The inner member has an inner edge. The device also includes a first snarecoil element that is formed as part of the inner member and includes an arcuate shaped first section that is connected to the inner edge of the inner member by a second section. The arcuate shaped first section has a free end that is attached to an inner surface of the outer cannula. The first snarecoil element is deformable such that the arcuate shaped first section moves between a rest position where the first section has an arcuate shape and a collapsed position where the first section has a substantially planar shape.

The retrieval device also includes a second snarecoil element that is formed as part of the inner member and includes an arcuate shaped first section that is connected to the inner edge of the inner member by a second section. The arcuate shaped first section has a free end that is attached to an inner surface of the outer cannula. The second snarecoil element is deformable such that the arcuate shaped first section moves between a rest position where the first section has an arcuate shape and a collapsed position where the first section has a substantially planar shape.

The first and second snarecoil elements are located opposite one another in the rest position and rotation of the inner tube relative to the outer cannula causes the first and second snarecoil elements to collapse toward a center of the outer cannula and assume the substantially planar shape with the tissue specimen being captured between the collapsed first and second snarecoil elements that are located in substantially parallel planes. The first and second snarecoil elements are oriented circumferentially in opposing positions, with the arcuate shaped first sections being located in the same plane which is oriented 90 degrees to the longitudinal axis of the outer cannula.

In another embodiment, a retrieval device for collecting a specimen includes an outer cannula member having an inner lumen and an inner member received within the inner lumen such that the inner member can rotate relative to the outer cannula. The inner member has an inner edge. The device has a first snarecoil element that is formed as part of the inner member and includes an arcuate shaped first section that is connected to the inner edge of the inner member by a second section. The arcuate shaped first section has a free end that is attached to an inner surface of the outer cannula. The first snarecoil element is deformable such that the arcuate shaped first section moves between a rest position where the first section has an arcuate shape and a collapsed position where the first section has a substantially planar shape.

A second snarecoil element is formed as part of the inner member and includes an arcuate shaped first section that is connected to the inner edge of the inner member by a second section. The arcuate shaped first section has a free end that is attached to an inner surface of the outer cannula. The second snarecoil element is deformable such that the arcuate shaped first section moves between a rest position where the first section has an arcuate shape and a collapsed position where the first section has a substantially planar shape.

The first and second snarecoil elements are oriented circumferentially in opposing positions, with the arcuate shaped first sections being located in two different planes each of which is oriented 90 degrees to the longitudinal axis of the outer cannula. Rotation of the inner tube relative to the outer cannula causes the first and second snarecoil elements to collapse toward a center of the outer cannula and assume a substantially planar shape with the first sections of the first and second snarecoil elements being adjacent one another in the collapsed positions such that as the snarecoil elements move toward the collapsed positions, a proximal edge of the first section of the first snarecoil element slides by a distal edge of the first section of the second snarecoil element resulting in a shearing of the tissue specimen that is located therebetween.

BRIEF DESCRIPTION OF THE DRAWING FIGURES

The foregoing and other features and advantages of the present invention will be more readily apparent from the following detailed description and drawings of the illustrative embodiments of the invention wherein like reference numbers refer to similar elements and in which:

FIG. 1 is a front and side perspective view of a specimen retrieval device according to a first embodiment and in a rest position;

FIG. 2 is a cross-sectional view taken along the line 2-2 (a plane that is perpendicular to a longitudinal axis of the needle) of FIG. 1;

FIG. 3 is a front and side perspective of the specimen retrieval device of FIG. 1 in an actuated position;

FIG. 4 is a cross-sectional view taken along the line 4-4 (a plane that is perpendicular to a longitudinal axis of the needle) of FIG. 3;

FIG. 7 is a front and side perspective view of a specimen retrieval device according to a second embodiment in a rest position;

FIG. 8 is a cross-sectional view taken along the line 8-8 (a plane that is perpendicular to a longitudinal axis of the needle) of FIG. 7;

FIG. 9 is a front and side perspective of the specimen retrieval device of FIG. 8 in an actuated position;

FIG. 10 is a cross-sectional view taken along the line 10-10 (a plane that is perpendicular to a longitudinal axis of the needle) of FIG. 9;

DETAILED DESCRIPTION OF EMBODIMENTS

Figure 5:
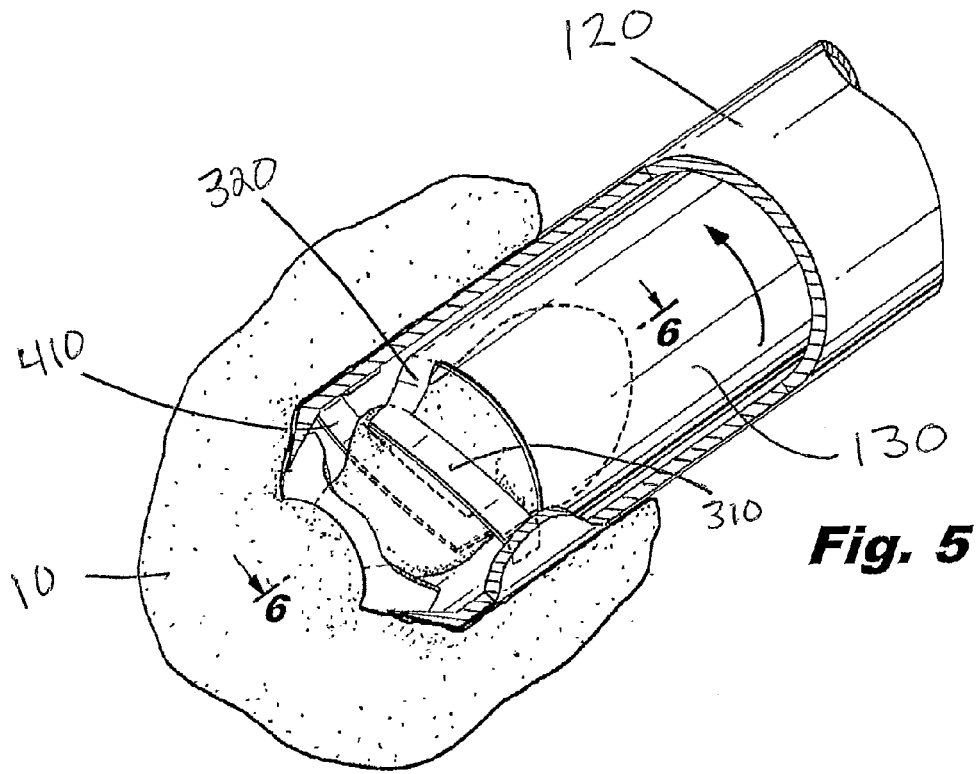
FIG. 5 is a front and side perspective view of the specimen retrieval device of FIG. 1 inserted into tissue and after being moved to the actuated position for collection of a specimen.

Referring to FIGS. 1-6, a retrieval device 100 (specimen retrieving and capturing device) of a snarecoil design is illustrated and is configured to retrieve a target specimen which can be in the form of a tissue specimen or a foreign material that is located in certain vascular or nonvascular spaces. To facilitate entry of the retrieval/capturing device 100 into vascular and nonvascular spaces or duct channels, the device 100 incorporates a catheter system 110. The catheter system 110 includes an outer catheter (outer cannula) 120 within which an inner member 130 is disposed and in particular, the inner member 130 can be in the form of a tube/catheter that is disposed within the outer cannula 120 and is movable relative thereto. In the case of where the inner member 130 and outer cannula 120 have cylindrical shapes, the outer diameter of the inner member 130 is thus less than the inner diameter of the outer cannula 120.

It will be appreciated that the construction of the catheter 100 of the present invention can vary depending upon the precise application. For example, in the example of a percutaneous soft tissue needle, the outer cannula 120 can take the form of a rigid tube. Alternatively, in the case of when the catheter 100 is part of a flexible system that is adapted to be used in conjunction with an endoscopic ultrasound or other similar instrument, the outer cannula 120 can take the form of a bendable catheter.

The inner member 130 is thus an elongated structure that is shaped and dimensioned to be received within an interior (lumen) 122 of the outer catheter 120. The outer catheter 120 is typically in the form of an elongated tube that has an open distal end 124 and an opposite proximal end (not shown) that can be an open end. It will be understood that in some cases, the proximal end of the outer catheter 120 can be partially closed or fully closed. The outer catheter 120 is a hollow structure with the interior 122 being in the form of an elongated bore or through channel formed the length of the outer catheter 120. The outer catheter 120 has an outer surface 127 and an opposite inner surface 129 that defines the bore 122.

As described in greater detail herein, the inner member 130 is designed and is positioned within the bore 122 so that it can be rotated within the outer catheter 120. The inner member 130 has an elongated structure and is defined by a distal end 132 and an opposing proximal end (not shown).

In accordance with the present invention, the inner member 130 has a snarecoil-like structure that is formed of a first snarecoil-like element 300 (a snarecoil segment or snarearc) and a second snarecoil-like element 400 (a snarecoil segment or snarearc). It will be appreciated that while the elements 300, 400 are described as being snarecoil-like, they do not have a true coil design and therefore do not have a measurable diameter. Instead and as described herein, the elements 300, 400 are arcuate in shape and are not defined by a diameter due to the elements not extending in a complete circumference.

More specifically, the inner member 130 includes an inner edge 131 that is close to the distal end 132 of the inner member 130. The inner edge 131 can be in the form of a continuous edge that has a circumferential shape and the first and second snarecoil elements 300, 400 extend distally beyond the inner edge 131 so as to define the distal end 132 of the inner member 130.

The first snarecoil element 300 is formed by a first section 310 that has an arcuate shape that is complementary to the arcuate shape of the inner surface of the outer catheter 120. In addition, it will be appreciated that the arcuate shape of the first section 310 is complementary or "in-line" with the circumferential shape of the inner member 130 itself. In other words, when viewing the inner member 130 from the end, the curved first section 310 is in-line with the curved body of the inner member 130. The first section 310 has a first end 312 that is fixedly attached to an inner surface of the outer catheter 120.

As shown in the figures, the first section 310 can be thought of as being an arcuate shaped finger that is attached at its free (first) end 312 to the inner surface of the outer catheter 120. The first section 310 is located in a plane that is at least generally parallel to the inner edge 131.

The first section 310 is connected to the inner edge 131 with a second section 320 that can be thought of as a connector section. The connector section 320 thus extends between the first section 310 and inner edge 131 connecting the first section 310 to the inner edge 131 in such a way that the first section 310 can move and flex as described in greater detail herein. The second section 320 can be thought of as being a finger or bridge that is perpendicular, in one embodiment, to both the inner edge 131 and the first section 310.

Since the first section 310 is spaced from the inner edge 131 by the second section 320, a space or slot 330 is formed between the first section 310 and the inner edge 131.

The first end 312 can be connected to the inner surface of the outer catheter 120 using any number of conventional techniques. For example, the first end 312 can be bonded or otherwise can be mechanically attached to the inner surface of the outer catheter 120. An adhesive or other material can be used to fixedly attach the first end 312 to the inner surface of the outer catheter 120. In addition, a physical structure such as a rivet or the like can be used to fixedly attach the first end 312 to the inner surface of the outer catheter 120.

The second snarecoil element 400 is formed by a first section 410 that has an arcuate shape that is complementary to the arcuate shape of the inner surface of the outer catheter 120. The first section 410 has a first end 412 that is fixedly attached to an inner surface of the outer catheter 120. In addition, it will be appreciated that the arcuate shape of the first section 410 is complementary or "in-line" with the circumferential shape of the inner member 130 itself. In other words, when viewing the inner member 130 from the end, the curved first section 410 is in-line with the curved body of the inner member 130.

As shown in the figures, the first section 410 can be thought of as being an arcuate shaped finger that is attached at its free (first) end 412 to the inner surface of the outer catheter 120. The first section 410 is located in a plane that is at least generally parallel to the inner edge 131.

The first section 410 is connected to the inner edge 131 with a second section 420 that can be thought of as a connector section. The connector section 420 thus extends between the first section 410 and inner edge 131 to connect the first section 410 to the inner edge 131 in such a way that the first section 410 can move and flex as described in greater detail herein. The second section 420 can be thought of as being a finger or bridge that is perpendicular, in one embodiment, to both the inner edge 131 and the first section 410.

Since the first section 410 is spaced from the inner edge 131 by the second section 420, a space or slot 430 is formed between the first section 410 and the inner edge 131.

The first end 412 can be connected to the inner surface of the outer catheter 120 using any number of conventional techniques. For example, the first end 412 can be bonded or otherwise be mechanically attached to the inner surface of the outer catheter 120. An adhesive or other material can be used to fixedly attach the first end 412 to the inner surface of the outer catheter 120. In addition, a physical structure such as a rivet or the like can be used to fixedly attach the first end 412 to the inner surface of the outer catheter 120.

The points of attachment of the two first ends 412, and 312 to the inner surface of the outer catheter 120 are at locations that are opposite one another (180 degrees apart) as best shown in the cross-sectional views of FIGS. 2 and 4.

In one embodiment, the lengths and/or the widths of the first sections 310, 410 are at least substantially the same with the first sections 310, 410 being offset from one another as described herein. Each of the illustrated first sections 310, 410 has a rectangular shape. The first sections 310, 410 have shorter circumferential/helical lengths compared to the typical snarecoils described in the present applicant's issued patents. This reduced length of the first sections 310, 410 (snarearcs) permits the snarecoil elements 300, 400, upon rotation of the inner member 130, to be translated in a direction towards the center of the inner member 130. In other words and as described in more detail herein, the rotation of the inner member 130 causes a deformation of the first sections 310, 410 such that the first sections 310, 410 assume a more flatted state (e.g., preferably assume an at least substantially planar orientation).

It will be appreciated that as the inner member 130 rotates, the first sections 310, 410 deform from arc configurations resulting in translation of each arc's location to a more central position that is within the center of the outer cannula 120.

It will be appreciated that the present snarearc design is based on the understanding that most previous snarecoil embodiments were helical and did not pass through the center portion of the inner tube after activation. Unlike Applicant's previous snarecoil designs where the snarecoil is wound down in that the diameter of the completely circular structure is reduced as the device is actuated, the present invention is different in that the snarecoil is formed of distinct, separate arcuate segments as opposed to a completely circular snarecoil and thus, the present snarecoil does not have a true defined diameter.

The snarearc (first section 310, 410) ostensibly becomes a plane after the rotation/deformation when it assumes the second collapsed or flattened position. In contrast, Applicant's prior snarecoil designs assume a configuration, after actuation (rotation) of the device, that is associated with a second diameter, while the snarearc (first section 310, 410) can never assume such a configuration, since in its second position it is linear and by definition, can not geometrically have a diameter. In contrast, the present invention is based on the objective that in certain situations, it is beneficial for the snarecoil to deform into the center of the inner tube 130.

FIG. 2 shows the opposing and arcuate nature of the first sections 310, 410 in the normal, rest position before rotation of the inner tube 310 relative to the outer catheter 120. FIGS. 3-4 show the snarecoil in the actuated position where the first sections 310, 410 (snarearcs) deform towards the center of the outer catheter 120 (substantially flatten out). Actuation of the snarecoil is achieved by rotating the inner tube 130 relative to the outer catheter 120 in the direction shown by arrow 135 in FIG. 3.

The snarecoil elements (first sections) 300, 400 rotate in the same direction and are also positioned in an "opposing" fashion for the snarecoil assembly to function properly. If the snarecoils 300, 400 are to deform and move to the central position of the inner tube 130 to form a pinching or clamping mechanism, the two snarecoils 300, 400 must be oriented circumferentially in opposing positions and also located in the same plane. The plane should be oriented 90° to the longitudinal axis of the device 100.

FIGS. 3 and 4 show the snarecoil elements 300, 400 in the actuated (deformed) position where the first sections 310, 410 are located in a facing, spaced relation, with each first section 310, 410 being at least substantially flat and thus in substantially parallel planes with a space 325 located between the first sections 310, 410. The space 325 represents the grasping or capture area of the device where a tissue sample or a foreign body is captured.

Figure 6:
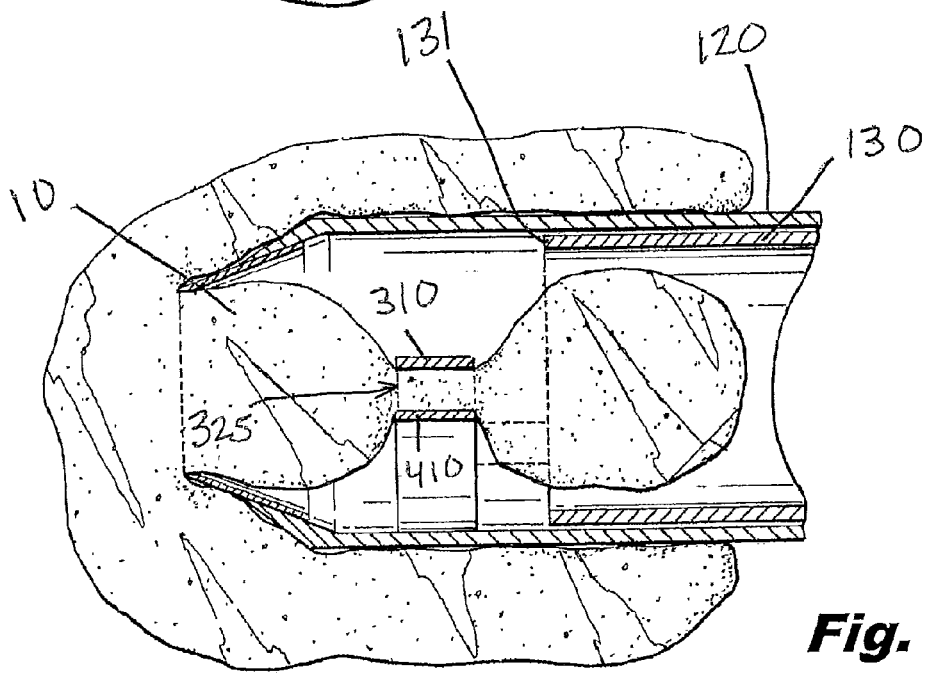
FIG. 6 is a cross-sectional view taken along the line 6-6 (a plane that is perpendicular to a longitudinal axis of the needle) of FIG. 5.
Figure 11:
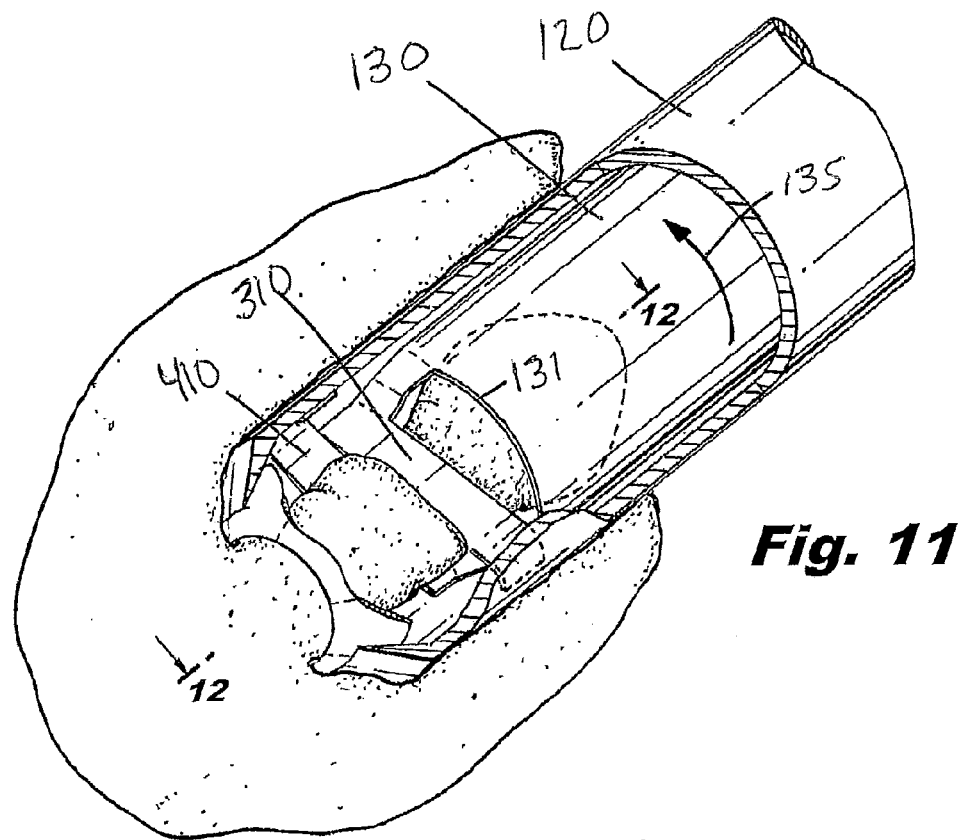
FIG. 11 is a front and side perspective view of the specimen retrieval device of FIG. 7 inserted into tissue and after being moved to the actuated position for collection of a specimen.
Figure 12:
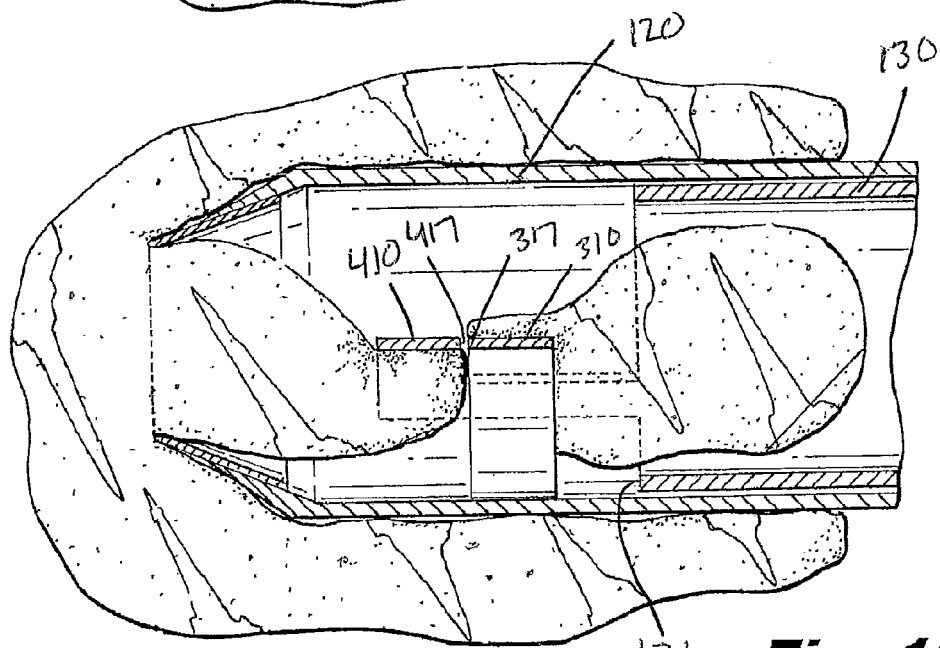
FIG. 12 is a cross-sectional view taken along the line 12-12 (a plane that is perpendicular to a longitudinal axis of the needle) of FIG. 11.

FIGS. 5 and 6 show the device 100 in use for collecting a tissue specimen. In particular, FIGS. 5 and 6 show the snarecoil elements 300, 400 in the actuated position with a tissue specimen 10 being captured within the space 325 and thus grasped and held by the collapsed snarecoil elements 300, 400. The collapsing snarecoil elements 300, 400 create a pinching action for capturing the tissue specimen 10.

It will be understood that the snarecoil-like elements 300, 400 are constructed such that the snarecoil elements 300, 400 have to be able to resume or nearly resume their non-deformed positions upon opposite rotation of the inner member 130.

FIGS. 7-12 show a retrieval device 500 (specimen retrieving and capturing device) of a snarecoil design according to a second embodiment. The retrieval device 500 is similar to the retrieval device 100 with the exception that the orientation of the snarecoil elements 300, 400 is different in the retrieval device 500. The retrieval device 500 is designed to provide a scissor-like shearing action for cutting the tissue specimen 10 to permit the tissue specimen to be collected.

As with the other embodiment, the snarecoil elements 300, 400 deform and move to the central position of the inner tube 130 and form a scissoring mechanism. The two snarecoil elements 300, 400 are oriented circumferentially in opposing positions and the snarecoil elements 300, 400 are located in two different planes each of which are oriented 90° to the longitudinal axis of the needle as shown in FIG. 7. Since a "scissor" can cut when the blades (in this case, the first sections 310, 410) are at different angles, the two snarecoil elements 300, 400 do not have to be orientated 180 degrees from each other, but could be positioned at another orientation say 120 or 140 degrees relative to each other. The relative positions of the snarearcs (first sections 310, 410) are determined by the relative circumferential positions of the snare connectors 320 and 420. For instance, if the connectors are 180 degrees from each other the snarecoil elements 300 and 400 would be orientated 180 degrees from each other. More generally if the connectors are a degrees from each other the snarecoil elements 300 and 400 would be orientated a degrees from each other, as the distal edge of 310, 317 and proximal edge of 410, 417 pass by each other with actuation. The two planes are parallel and adjacent to each other so that a proximal edge (cutting edge) 417 of the first section 410 of the distal snarecoil element 400 intimately slides by a distal edge (cutting edge) 317 of the first section 310 of the proximal snarecoil element 300 when each of the snarecoil elements 300, 400 are deformed into a linear structure traversing the center of the inner tube 130.

In other words, as the inner tube 130 is rotated in one direction (arrow 135), the snarecoil elements 300, 400 begin to collapse and move inward toward the center of the outer catheter 120 such that they assume the substantially flat orientation.

In the device 500, the first and second snarecoil elements 300, 400 are similar to those snarecoil elements 300, 400 of the device 100; however, there are several important differences between the snarecoil elements of the two devices 100, and 500. In particular, first and second snarecoil elements 300, 400 are spatially offset from one another such that one of the snarecoil elements 300, 400 is closer to the distal end 122 of the outer catheter 120. As shown in the embodiment of FIGS. 7-10, the second snarecoil element 400 is closer to the distal end 122 of the outer catheter 120. The offsetting of the first sections 310, 410 requires the spaces 330, 430 to be of different size since when the first section 310 deforms and flattens in response to rotation of the inner member 130, the first section 310 at least partially occupies the space 430. The first sections 310, 410 can be offset from one another by forming the connector section 420 to have a longer length, thereby spacing the first section 410 further from the first edge 131.

Given the above described movements of the snarecoil elements 300, 400, the connecting members 320, 420 (e.g., forward projecting tab-like structures) have structure and material characteristics which allow the snarecoil elements 300, 400 (snarearcs) to "flatten out" or deform from an arcuate confirmation in the normal, rest position to a more linear confirmation upon rotation of the inner tube 130 relative to the outer catheter 120. The connecting members (second sections 320, 420) do not necessarily need to deform themselves or lose their circumferential positions relative to the inner tube 130 but must be flexible enough to allow the first sections 310, 410 to deform into a more linear structure ("flattened position"). In some embodiments, the flexibility of the second sections 320, 420 can allow the second sections 320, 420 to serve as almost a pivoting member.

It will also be appreciated that in order for the snarecoil to behave in the manner described herein, the snarecoil elements 300, 400 have a certain length, configuration, deformability and malleability. In addition, the snarecoil elements 300, 400 have material characteristics that will allow it to regain its original confirmation once the inner tube 130 is rotated back to its original position.

EXAMPLE

To reduce the diameter of a typical helical snarecoil (see the present applicant's prior U.S. patents mentioned herein) to zero would be theoretically impossible although from a practical point of view could nearly be achievable. In other words one rotation of a helical snarecoil will result in the diameter decreasing 50%. A second rotation will decrease the diameter 50% of the prior 50% or decreasing it a further 25%. Therefore two rotations will result in a decrease in the diameter of 75% compared with the original diameter. The third rotation will decrease the residual 25% of the diameter an additional 50% to a diameter that is 12.5% of the original, and overall the diameter will have decreased 87.5%, yet the diameter still will not have decreased a true 100% from the original diameter. From a mathematical point of view, the diameter can never actually be zero but can only approach it asymptotically.

As mentioned above, the present invention is based on the understanding that to grab, cut or deform certain tissues, especially soft tissues, that tend to collapse when pressure is applied by the snarecoil, the snarecoil elements 300, 400 must deform into the center portion of the inner tube 130.

Such a deformation is possible if the length of the snarecoil is reduced, so that a portion of a snarecoil element or snarearc (section 310, 410) is capable of collapsing into a flattened state. The circumference of a circle equals $\pi d$, where d is the diameter of the circle. Since $\pi$ is approximately equal to 3, the equation reduces to C=3d, approximately. Therefore, approximately ⅓ of the length of the circumference is equal to the diameter of a circle.

These observations are relevant to the concept of deforming a portion of a snarecoil into a linear structure that passes through the center of the inner tube 130. If the arc of a snarecoil (i.e., section 310, 410) is to be rotated and deformed into a linear element that traverses the center of the inner tube, then the arc can not be any longer than C/3 or more specifically $C/\pi$. If the arc is shorter than $C/\pi$, the snarecoil material should be malleable or stretchable so that as it is deformed the arc can lengthen to a diameter that will then equal the length d.

The snarecoil elements 300, 400 can be designed in view of the foregoing observations and teachings.

However, the foregoing example is not limiting of the present invention and alternative snarecoil designs can be created. For example, the diameter can be represented as a percentage of the full diameter described by $C/\pi$. For example there can be a configuration in which a diameter is constructed that is 80% or 70% of the full diameter (to take advantage of its elasticity) and in such a case, the equations would be 0.80C/π and 0.70C/π, respectively. Alternatively the length of the snarecoil can be longer then C/π, i.e., a multiple of C/π in which the multiplier is greater than 1.

It will also be appreciated that the retrieval devices can be constructed such that the initiating points of the snarecoils are less than 180 degrees from each other and therefore, the present invention is not limited to the situation in which the initiating points are 180 degrees apart as shown in the figures. Conversely, there can be situations in which the initiating points of the snarecoils are less than 180° from each.

In addition, there can be configurations in which there are multiple snareares incorporated into the assembly. For instance, a retrieval device can be three snarecoils each having attachment points to the inner tube 120° apart from the others or a retrieval device configuration with four (4) snarecoils each having an attachment to the inner tube 90° apart from the other.

It will also be appreciated that the embodiments that are shown include two snarearcs (e.g., first sections 310, 410) but that a multiplicity of snarearcs can be incorporated into the snarecoil or snarearc assembly. In other words there conceivably could be many snarearcs sequentially attached to the distal aspect of the inner tube with their opposite ends sequentially and circumferentially attached to the inner aspect of the inner tube, so that rotating the inner tube will result in a deformation of numerous snarearcs into linear elements across the center of the inner tube. If the snarearcs are made of relatively thin materials such as wire-like structures then the deformation of a multiplicity of snarearcs could result in the formation of a web like structure that could close off the distal aspect of the inner tube.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different points set forth below may be combined in various ways in further accordance with the present invention.

What is claimed is:

1. A retrieval device for collecting a specimen comprising:
   an outer cannula having an inner lumen;
   an inner member received within the inner lumen such that the inner member can rotate relative to the outer cannula, the inner member having an inner edge;
   a first snarecoil element that is formed as part of the inner member and includes an arcuate shaped first section that is connected to the inner edge of the inner member by a second section, the arcuate shaped first section having a free end that is attached to an inner surface of the outer cannula, the first snarecoil element being deformable such that the arcuate shaped first section moves between a rest position where the first section has an arcuate shape and a collapsed position where the first section has a planar shape; and
   a second snarecoil element that is formed as part of the inner member and includes an arcuate shaped first section that is connected to the inner edge of the inner member by a second section, the arcuate shaped first section having a free end that is attached to an inner surface of the outer cannula, the second snarecoil element being deformable such that the arcuate shaped first section moves between a rest position where the first section has an arcuate shape and a collapsed position where the first section has a planar shape;
   wherein the first and second snarecoil elements are located opposite one another in the rest position and rotation of the inner tube relative to the outer cannula causes the first and second snarecoil elements to collapse toward a center of the outer cannula and assume the collapsed positions with a space formed therebetween for receiving and capturing the tissue specimen between the collapsed first and second snarecoil elements that are located in parallel planes.

2. The retrieval device of claim 1, wherein the free ends of the first sections of the first and second snarecoil elements are located at least 180 degrees apart from one another.

3. The retrieval device of claim 2, wherein the free ends of the first sections are attached to the inner surface with fasteners.

4. The retrieval device of claim 1, wherein lengths of the second sections as measured along a longitudinal axis of the inner member are the same.

5. The retrieval device of claim 1, wherein the free ends of the first sections are attached to the outer cannula at locations spaced from a distal end of the outer cannula.

6. The retrieval device of claim 1, wherein each arcuate shaped first section has a degree of curvature less than 180 degrees.

7. The retrieval device of claim 1, wherein the second sections are located at least 180 degrees apart.

8. The retrieval device of claim 1, wherein a slot is formed between each first section and the inner edge of the arcuate shaped first section, the slot having a first open end and being closed at a second end by the respective second section.

9. The retrieval device of claim 1, wherein a length of the arcuate shaped first section of each of the first and second snarecoil elements is equal to C/π, where C is a circumference of the inner member.

10. A retrieval device for collecting a specimen comprising:
    an outer cannula having an inner lumen;
    an inner member received within the inner lumen such that the inner member can rotate relative to the outer cannula, the inner member having an inner edge;
    a first snarecoil element that is formed as part of the inner member and includes an arcuate shaped first section that is connected to the inner edge of the inner member by a second section, the arcuate shaped first section having a free end that is attached to an inner surface of the outer cannula, the first snarecoil element being deformable such that the arcuate shaped first section moves between a rest position where the first section has an arcuate shape and a collapsed position where the first section has a planar shape; and
    a second snarecoil element that is formed as part of the inner member and includes an arcuate shaped first section that is connected to the inner edge of the inner member by a second section, the arcuate shaped first section having a free end that is attached to an inner surface of the outer cannula, the second snarecoil element being deformable such that the arcuate shaped first section moves between a rest position where the first section has an arcuate shape and a collapsed position where the first section has a planar shape;
    wherein the first and second snarecoil elements are oriented circumferentially in opposing positions, with the arcuate shaped first sections being located in two different planes each of which is oriented 90 degrees to a longitudinal axis of the outer cannula, wherein rotation of the inner tube relative to the outer cannula causes the first and second snarecoil elements to collapse toward a center of the outer cannula and assume the collapsed positions with the first sections of the first and second snarecoil elements being adjacent one another in the collapsed positions such that as the snarecoil elements move toward the collapsed positions, a proximal edge of the first section of the first snarecoil element slides by a distal edge of the first section of the second snarecoil element resulting in a shearing of the tissue specimen that is located therebetween.

11. The retrieval device of claim 10, wherein the free ends of the first sections of the first and second snarecoil elements are located at least 180 degrees apart from one another but are located in different adjacent transverse planes.

12. The retrieval device of claim 11, wherein the free ends of the first sections are attached to the inner surface with fasteners.

13. The retrieval device of claim 10, wherein lengths of the second sections as measured along a longitudinal axis of the inner member are the same.

14. The retrieval device of claim 10, wherein the free ends of the first sections are attached to the outer cannula at locations spaced from a distal end of the outer cannula.

15. The retrieval device of claim 10, wherein each arcuate shaped first section has a degree of curvature less than 180 degrees.

16. The retrieval device of claim 10, wherein the second sections are located at least 180 degrees apart but in different adjacent planes.

17. The retrieval device of claim 10, wherein a slot is formed between each first section and the inner edge of the arcuate shaped first section, the slot having a first open end and being closed at a second end by the respective second section.

18. The retrieval device of claim 10, wherein the proximal edge and distal edge of the first sections of the first and second snarecoil elements respectively are sharpened edges.

19. A method for collecting a specimen comprising the steps of:

introducing a retrieval device to a target location at which the specimen is located, the retrieval device having an outer cannula and a hollow inner member received within the outer cannula such that the inner member can rotate relative to the outer cannula, the inner member having associated therewith a first snarecoil element and a second snarecoil element spaced from and free of contact with the first snarecoil element, wherein each of the first and second snarecoil elements has a deformable arcuate shaped first section that is attached to the inner member at a free end thereof, wherein the first and second snarecoil elements maintain the arcuate shape in a rest position;

receiving the specimen within an open distal end of the outer cannula and into the inner member such that a portion of the specimen lies between the arcuate shaped first sections in the rest position; and rotating the inner member relative to the outer cannula to cause the first and second snarecoil elements to collapse toward a center of the outer cannula, thereby causing each of the first sections to assume a planar shape resulting in the specimen being capture between the first and second snarecoil elements.

20. The method of claim 19, wherein the first and second snarecoil elements are located directly opposite one another and the step of rotating the inner member relative to the outer cannula causes the collapsed first and second snarecoil elements to be located in parallel planes with the specimen located therebetween.

21. The method of claim 19, wherein the first and second snarecoil elements are oriented circumferentially in opposing positions, with the deformable arcuate shaped first sections being located in two different planes each of which is oriented 90 degrees to a longitudinal axis of the outer cannula, wherein the step of rotating the inner tube relative to the outer cannula causes the first and second snarecoil elements to collapse toward a center of the outer cannula and assume the planar shape with the first sections of the first and second snarecoil elements being adjacent one another such that they lie in the same plane, thereby shearing the specimen.

* * * * *